United States Patent

Lundberg et al.

Patent Number: 6,149,639
Date of Patent: Nov. 21, 2000

[54] ABSORBENT ARTICLE WITH MALE AND FEMALE LOCKING ELEMENTS

[75] Inventors: Hakon Lundberg, Sävedalen; Anders Gustafsson, Billdal; Anna Karin Jönbrink, Lerum, all of Sweden

[73] Assignee: SCA Hygiene Products AB, Gothenburg, Sweden

[21] Appl. No.: 08/973,710

[22] PCT Filed: Jun. 25, 1996

[86] PCT No.: PCT/SE96/00836

§ 371 Date: Jan. 5, 1998

§ 102(e) Date: Jan. 5, 1998

[87] PCT Pub. No.: WO97/02796

PCT Pub. Date: Jan. 30, 1997

[30] Foreign Application Priority Data

Jul. 7, 1995 [SE] Sweden .................................. 9502491

[51] Int. Cl.[7] .............................. A61F 13/15; A61F 13/20
[52] U.S. Cl. .............................. 604/386; 24/590; 24/589; 604/385.01
[58] Field of Search .................................. 604/385.1, 366, 604/391, 385.07; 24/590, 589, 627, 616, 114.4, 615, 108, 107

[56] References Cited

U.S. PATENT DOCUMENTS

| | | |
|---|---|---|
| 2,558,215 | 6/1951 | Habig et al. .............................. 604/386 |
| 3,479,703 | 11/1969 | Embry ........................................ 24/107 |
| 4,577,376 | 3/1986 | Clendinen .................................. 24/624 |
| 4,726,807 | 2/1988 | Young et al. . |
| 4,785,508 | 11/1988 | Takeda .................................... 24/114.4 |
| 4,825,516 | 5/1989 | Ackermann et al. .................. 24/114.4 |
| 4,872,871 | 10/1989 | Proxmire et al. . |
| 4,895,569 | 1/1990 | Wilson et al. .......................... 604/386 |
| 5,219,342 | 6/1993 | Hatch et al. ............................ 604/385 |
| 5,236,429 | 8/1993 | Widlund . |
| 5,269,776 | 12/1993 | Lancaster et al. . |

FOREIGN PATENT DOCUMENTS

| | | |
|---|---|---|
| 0 197 220A1 | 10/1986 | European Pat. Off. . |
| 0 215 408A2 | 3/1987 | European Pat. Off. . |
| 91/3734 | 4/1993 | Islamic Rep. of Iran . |
| 17452 | of 1913 | United Kingdom ..................... 24/627 |
| 2 288 314 | 10/1995 | United Kingdom . |

*Primary Examiner*—Mark O. Polutta
*Attorney, Agent, or Firm*—Burns, Doane, Swecker & Mathis, L.L.P.

[57] ABSTRACT

The present invention relates to an absorbent article fastener device and to a method for its manufacture. The invention relates to locking elements which are formed with the aid of subpressure, and which are applied fully or partially in-line with the manufacture of an absorbent article. The inventive absorbent article fastener device is designed so that the fastener can only be fastened in one specific orientation, with the fit of the article on the wearer being achieved with the aid of elastic devices.

9 Claims, 4 Drawing Sheets

ABSORBENT ARTICLE WITH MALE AND FEMALE LOCKING ELEMENTS

BACKGROUND

The present invention relates to absorbent article fastener means and to a method of manufacturing said means. The fastener means are used preferably to fasten or close an absorbent article, such as a diaper, an incontinence guard or like article. The fastener means is effective in fulfilling the desired function of the absorbent articles with regard to sealing of said articles at their leg openings and waist part, and also in ensuring a good fit. The fastener means enables the article to be opened and re-closed repeatedly.

TECHNICAL BACKGROUND

Many different kinds of absorbent article fastener means are available commercially. One example of such fastener means is found described in U.S. Pat. No. 5,236,429, in the which absorbent article is fastened with the aid of a number of fastener tabs which are fastened within a particular tape-receiving area designed to enable the fastener tabs to be loosened from and refastened in the area repeatedly. This enables the fit of the absorbent article on the wearer to be adjusted and also enables the article to be inspected repeatedly with regard to its soiled state. Also available commercially are different products in which the fastener means have the form of so-called touch-and-close fasteners, e.g. Velcro® tape, which are used in a similar manner to the aforesaid fastener tabs. Also known in the art are fastener means which use conventional buttons, press studs and like devices. U.S. Pat. No. 5,269,776 describes a diaper which includes fastener means comprised of discrete pieces of material that are provided with a multiple of circular bosses. These bosses are comprised of two types of fastener elements, a male element and a female element, of similar design but with a small difference in size, therewith enabling the male element to be pressed into the female element to produce a locking effect. When respective female and male elements are mutually positioned on the discrete pieces of material, the mutual positioning of the discrete pieces of material provided with the locking elements can be varied so as to adjust the fit of the article on the wearer in accordance with requirements. The aforesaid locking elements may be produced by vacuumforming heated plastic film or by rolling plastic material between profiled rolls.

TECHNICAL PROBLEMS

One problem with the use of fastener means of the kind described above with reference to U.S. Pat. No. 5,269,776 resides in positioning the discrete pieces of material provided with locking elements correctly on the absorbent article in conjunction with its manufacture. Furthermore, when adjusting the position of an absorbent article on the wearer, there is a danger of displacing the discrete pieces of material provided with the locking elements laterally in a vertical and/or sideways direction, therewith impairing function and/or reducing comfort, for instance because the absorbent body is wrongly located, because the fastener means become located at vulnerable places, such as the iliac crests, or because the elastic cuts into the body, etc. Another problem encountered with this type of locking element is that pre-formed material from which the discrete pieces of material provided with pre-formed locking elements are obtained is often supplied and stored in the form of reels or stacks which require a large amount of space, because the locking elements extend at right angles to the normal plane of the ultimate discrete material pieces. In order to achieve an optimal function, the fastener means must be produced from a material which has a given rigidity or stiffness, which in turn enhances the risk of chafing and impaired comfort, among other drawbacks. Another problem with this type of fastener means is that powder, creams and the like are liable to adhere to the locking elements and reduce the friction engendered thereby, therewith impairing the locking ability of the coacting male and female elements.

When using fastener means that consist in mutually separate fastener elements, such as press studs for instance, another problem is that these elements must be attached to the absorbent article in a manner which will prevent a child loosening the elements and putting them into its mouth, with disastrous consequences. Small parts also make manufacture difficult.

SUMMARY OF THE INVENTION

The invention is based on the fact that if two units that are to be locked together will only fit with one another in one single way, it is impossible to mutually connect these units in a mutually incorrect position. However, this mutual position is of no interest when the locking elements used are wrongly positioned on the absorbent article. The present invention provides fastener means for securing an absorbent article, such as a diaper, an incontinence guard or like article, wherein the fastener means include mutually coacting parts in the form of female elements and male elements which fit into said female elements and which when locking the fastener means are pressed into a respective female element and there retained by friction forces and which are also held firmly by a so-called snap-function, i.e. by virtue of the mutual configuration of the elements, wherein the female element has an internal form of such narrowness in at least one location therein as to cause temporary elastic deformation when the male element is pressed into the female element, whereafter the elements return to their respective original shapes and are thus locked together.

The fastener means comprise discrete pieces of material, preferably thermoplastic material, where each discrete piece of material is provided with the locking elements in a configuration and/or male and female element distribution respectively, or size variation such that it can only be fastened to its associated receiving discrete piece of material in one single way. This design of the fastener means is possible when an effective fit of the absorbent article around the wearer is achieved solely with the aid of elastic devices, and hence no adjustments to the fastening positions of the fastener means on the absorbent article are required. Furthermore, the absorbent article will be placed more easily in the correct position on the wearer. By using raw material, preferably thermoplastic raw material, from which discrete pieces of material provided with locking elements are then formed, either during or in immediate connection with the manufacture of the absorbent article, the raw material can be supplied in the form of compact reel material. The present invention solves the problem of correctly positioning the fastener means as a whole on absorbent articles, by producing the fastener means, or at least by applying said fastener means, on the articles synchronously with the manufacture of the absorbent article.

In addition to a conventional homogenous state, the raw material may also be provided in a state in which certain parts of the material have a modified flexural strength. By appropriate positioning of these regions in the remainder of the manufacturing process, there are produced discrete pieces of material provided with locking elements with which the locking ability remains unchanged while, at the same time, the discrete pieces of material will be less rigid when seen as a whole, due to the presence of the regions of preferably reduced flexural rigidity. Alternatively, the flexural rigidity of the pieces of material can be modified, normally reduced, within certain regions during the manufacturing process or immediately prior to the process, preferably by mechanical, thermal or chemical influences. In none of the aforesaid two cases are the discrete pieces of material divided into smaller units, since large units are desirable in order to eliminate the risk of children being exposed to danger, for instance to choking by swallowing small parts freed from the absorbent article.

The invention also includes an embodiment in which nonwoven material is present in a laminate structure from which locking elements are formed, said nonwoven material increasing the friction between respective female and male elements when locking the fastener means, thereby enhancing the locking effect. In addition, locking elements that comprise nonwoven material will be less sensitive to the effect of powder, creams and fluids. In this regard, the nonwoven material may form a layer present in the absorbent article as a whole. However, the use of smaller pieces which only cover the actual fastener means or parts thereof is conceivable within the scope of the inventive concept. The use of nonwoven material also enhances the softness of the article against the skin, and imparts a visual impression of softness to the product, which is considered to be an attractive impression.

DETAILED DESCRIPTION OF THE INVENTION

Figure 1A:
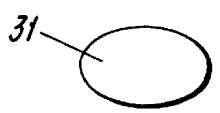
FIG. 1(a)–(h) illustrates a number of different exemplifying embodiments of the locking elements, as seen at right angles to the normal plane of the discrete piece of material.
Figure 1B:
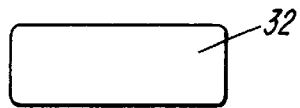
Figure 1C:
Figure 1D:
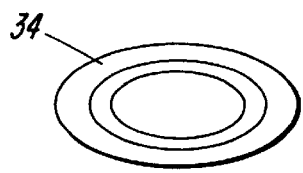
Figure 1E:
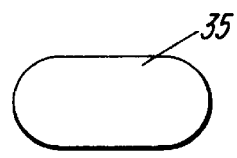
Figure 1F:
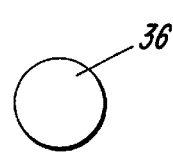

FIG. 1(a)–(h) illustrates a number of preferred embodiments of single locking elements as seen at right angles to the perpendicular plane of the discrete piece of material. Of the locking elements shown, in FIG. 1(a), the element 31 has a elliptical shape, in FIG. 1(b), the element 32 has a rectangular shape, the in FIG. 1(c) element 33 has a square shape, in FIG. 1(d), the element 34 has a sunken elliptical configuration, which will be more easily understood with the aid of the element 41 shown in FIG. 2(c), where the element 34 is shown in cross-section turned through 90°. The illustrated element 35 as shown in FIG. 1(e) has the shape of a square combined with segments of a circle, and the element 36 as shown in FIG. 1(f) has a circular shape. It will be understood, that the locking elements may have any one of an infinite number of shapes without departing from the concept of the invention that two similar elements having a small difference in size can be pressed together to achieve a locking effect, a so-called snap-effect. As before mentioned, the slightly smaller so-called male element is pressed into the so-called female element, wherein at least one of said elements consists in a material that has a given degree of elasticity.

Figure 1G:
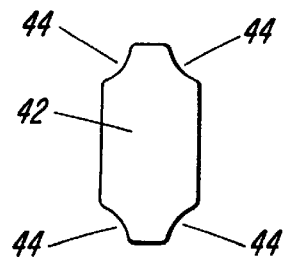
Figure 1H:
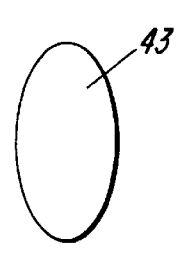

The female and male elements need not have precisely the same form, but may have mutually different forms. FIG. 1(g) shows an example of a male element 42 which has recesses or notches 44 in its four corners. This male element 42 is intended to fit into a female element 43, shown by the side of the male element 42 in FIG. 1(g). The female element 43 as shown in FIG. 1(h) lacks corresponding notches or recesses. Without limiting the invention to any precise theory, it is believed that the indented or recessed regions of the male element 42 can be deformed to facilitate insertion of the male element 42 in the female element 43. It is further believed that by indenting or recessing the corners of an elongated male element, such as the male element 42, the locking force will be greater in the transverse direction of the locked male and female elements than in the longitudinal direction. As a consequence it will be easier to release the female element from the male element in the longitudinal direction, than in the transverse direction. With this type of fastener elements you could arrange the male and female elements in any suitable direction depending on in which direction of the absorbent article you want the male and female fastener elements to engage one another with the greatest force while at the same time being able to be released from one another as easily as possible in another direction, preferably a direction at right angle to the one first mentioned. Preferably the male and female elements 42,43 will be arranged with their longitudinal dimension in the longitudinal direction of the absorbent article on which they are applied.

Figure 2A:
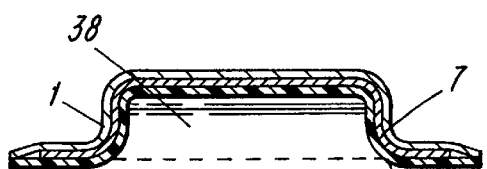
FIG. 2(a)–(e) is a cross-sectional view of some of the embodiments shown in FIG. 1, rotated through 90° in relation thereto.
Figure 2B:
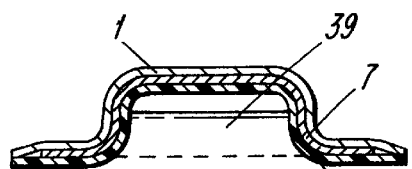
Figure 2C:
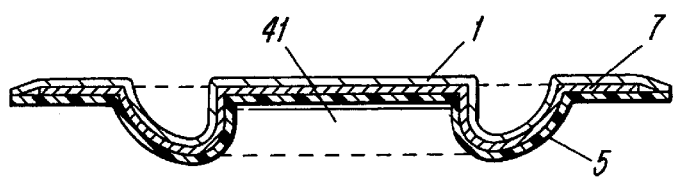
Figure 2D:
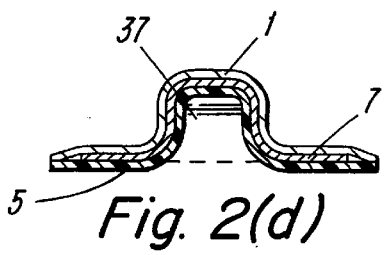
Figure 2E:
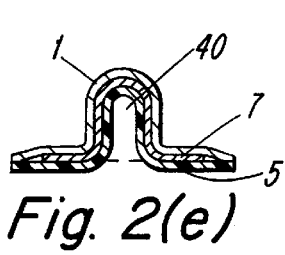

FIG. 2(a)–(e) illustrates a number of preferred exemplifying locking elements in cross-section and from one side in which the locking elements 7 are disposed between a web of liquid-impermeable material 5 and a web of non-woven material 1, i.e. seen in a direction which is turned through 90° in relation to the directions in FIGS. 1(a)–(h). For instance, the element 41 in FIG. 2(c) illustrates the locking element 34 of FIG. 1(d) turned through 90°. The locking elements 37–40 are shown in cross-section in order to show the form which acts positively on the locking effect achieved with the locking elements. In the case of one preferred embodiment, the locking elements of the inventive fastener means are produced by sucking parts of discrete material pieces into air-permeable moulds, therewith to form cavities by vacuum-forming, wherewith the material need only be heated to improve its mouldability. When forming of the locking elements in accordance with the present invention is carried out in-line with the remainder of the absorbent article manufacturing process, positioning of the locking elements will be synchronized with the remainder of the article manufacturing process. This process will be explained in more detail below, with reference to a number of exemplifying embodiments.

Figure 3:
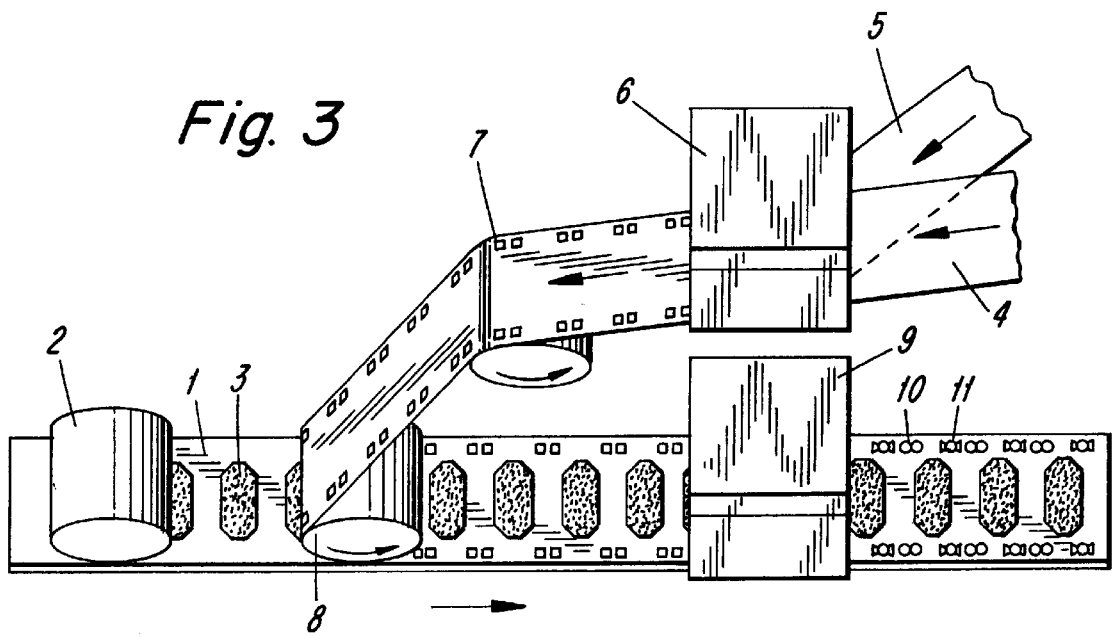
FIG. 3 is a schematic illustration of one method of producing an inventive fastener means.

FIG. 3 illustrates schematically a first preferred embodiment of a method of manufacturing absorbent articles provided with the preferred locking element. In this case, the outer layer 1 of the ultimate absorbent article is comprised of nonwoven material delivered to a mat-forming unit 2. Absorbent bodies 3 of preferably fibrous material are also placed on the layer 1 in the unit 2. The numeral 4 identifies the web of material in which the locking elements are to be formed, this web of material being delivered to a forming and applying device 6, where the discrete pieces of material 7 are produced. Also delivered to the device 6 is a material web 5 comprised preferably of liquid-impermeable plastic material which is to form the backing sheet of the absorbent article. The discrete material pieces 7 are applied to the web 5 in the device 6, preferably on that side of the web 5 which will ultimately be turned towards the layer 1, meaning that the discrete material pieces 7 will be located between the layer 1 and the web 5 in a finished preferred embodiment of an inventive absorbent article. The material web 5 and the discrete material pieces 7 are joined together with the layer 1 provided with absorbent bodies 3 in the joining and assembling station 8. The locking elements 10, 11 are then formed in the unit 9, wherein vacuum-forming is the technique preferably applied, in which both the male locking elements 11 and the female locking elements 10 are formed. These elements are given a configuration within the pieces 7 such that locking can only be effected in one specific way. Naturally, the described embodiment will also include the laying-out of elastic devices, the cutting-out of finished articles, etc., these manufacturing stages being purposely omitted both here and in the following embodiments, since a description of these manufacturing stages will not facilitate an understanding of the invention. It should be emphasized in connection with the description of the preferred embodiment that when the discrete material pieces 7 are placed between the layer 1 and the web 5, as in the case of the described embodiment, friction is increased and the locking effect between the locking elements 10 and 11 is enhanced due to the presence of the nonwoven material. Furthermore, the locking effect afforded by the locking elements is less vulnerable to the influence of powder, creams or fluids. The use of nonwoven material also enhances the softness of the absorbent article, and therewith also wearer comfort. Nonwoven material should also be used in the embodiments described below, to enhance the locking effect of the locking elements, this material either being in the form of completely covering layers, or in the form of pieces of material which cover only the locking elements or parts thereof.

Figure 4:
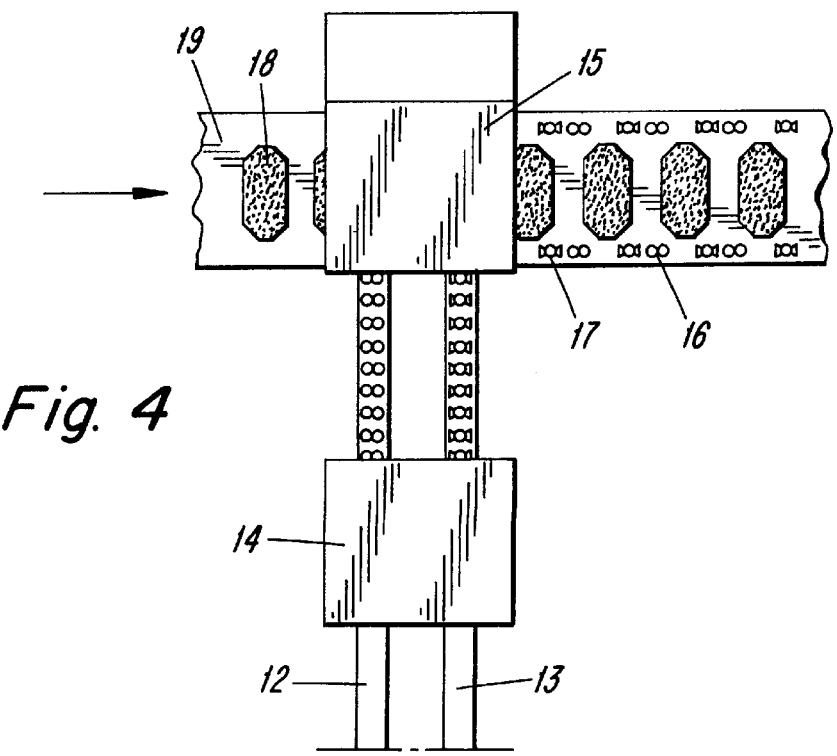
FIG. 4 is a schematic illustration of an embodiment corresponding to the embodiment of FIG. 3, but where the material is provided with locking elements prior to being clipped into discrete pieces.

FIG. 4 illustrates schematically a second preferred embodiment of a method of producing absorbent articles provided with the preferred locking elements. In this case, the locking elements are formed separately in a vacuum-forming device 14 to which raw material is delivered in the form of strips made preferably of thermoplastic material 12, 13, these strips being delivered to a forming-and-applying module 15 after being vacuum-formed. The strips 12, 13 are brought to a desired form in the module 15, for instance by clipping the strips, whereafter the discrete material pieces 16, 17 are applied to the absorbent article during its manufacture. The discrete pieces. 16, 17 are provided with male locking elements or female locking elements, which are thus applied externally to the laminate 19 consisting of surface material, preferably nonwoven material, and backing sheet material, preferably liquid-impervious plastic material. In this stage of manufacture, the absorbent bodies 18 and possibly also the elastic which is to be included in the finished absorbent articles have already been mounted on the absorbent articles under manufacture and are thus encapsulated in the laminate 19. After having applied the discrete pieces of material 16, 17 provided with locking elements, the absorbent articles under manufacture are transported to a finishing station and a packaging station.

The embodiments illustrated in FIGS. 3 and 4 are intended for so-called transverse production, i.e. production in which the manufactured products are advanced through the manufacturing machine with their long sides extending transversely to their direction of movement through the machine. Naturally, the invention can just as well be applied in these embodiments for so-called lengthwise production, in which the long sides of the products extend in their direction of movement through the machine.

Figure 5:
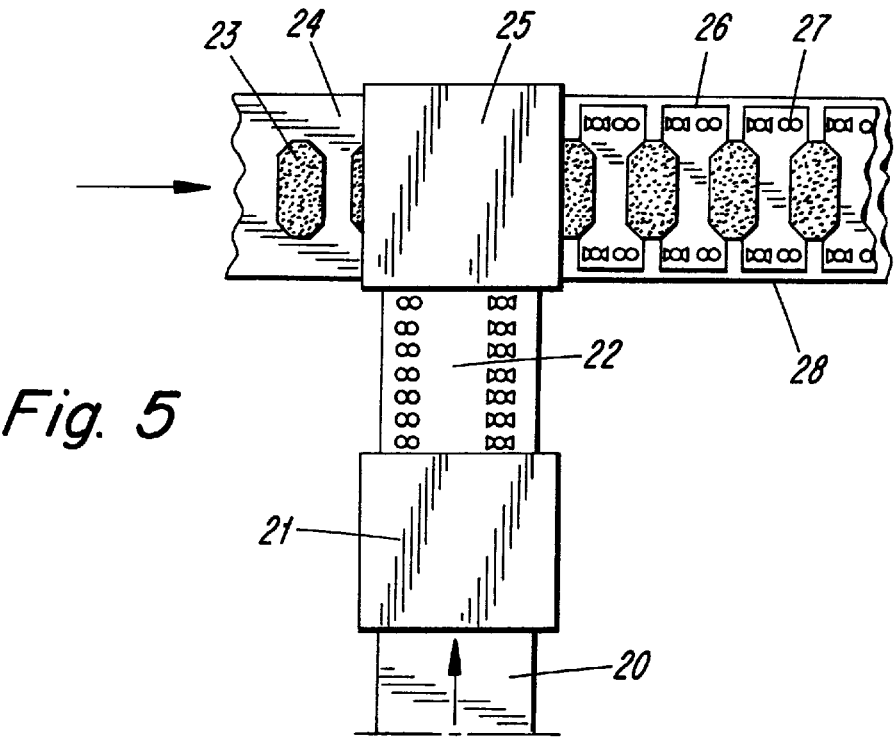
FIG. 5 illustrates schematically a variant of the embodiment shown in FIG. 4.

FIG. 5 illustrates a further preferred embodiment of the invention, similar to the embodiment illustrated in FIG. 4. The Figure shows an absorbent body 23 enclosed in a laminate 24 which is comprised of a liquid-permeable surface material which is intended to lie proximal to the wearer's skin in use, and a liquid-impermeable backing sheet. The raw material 20 from which the discrete pieces of material 26 are formed and in which the female locking elements 27 and the male locking elements 28 are to be formed, is delivered to a forming plant 21, preferably a vacuum-forming plant in which the different locking elements are formed. The now treated strip of material 22 is thereafter transported to a forming-and-applying station 25, in which the pieces of material 26 are shaped, e.g. by clipping, and applied to the laminate 24. In this stage of the manufacturing process, the discrete pieces of material 26 now applied to the laminate are provided with two separate arrays of locking elements 27 and 28 respectively. These material pieces 26 are separated in the subsequent working process, when the ultimate absorbent article is formed into separate products. In this regard, the separate ultimate absorbent articles may be alternately rotated through 180° prior to separation, which provides better use of the material among other things.

Figure 6:
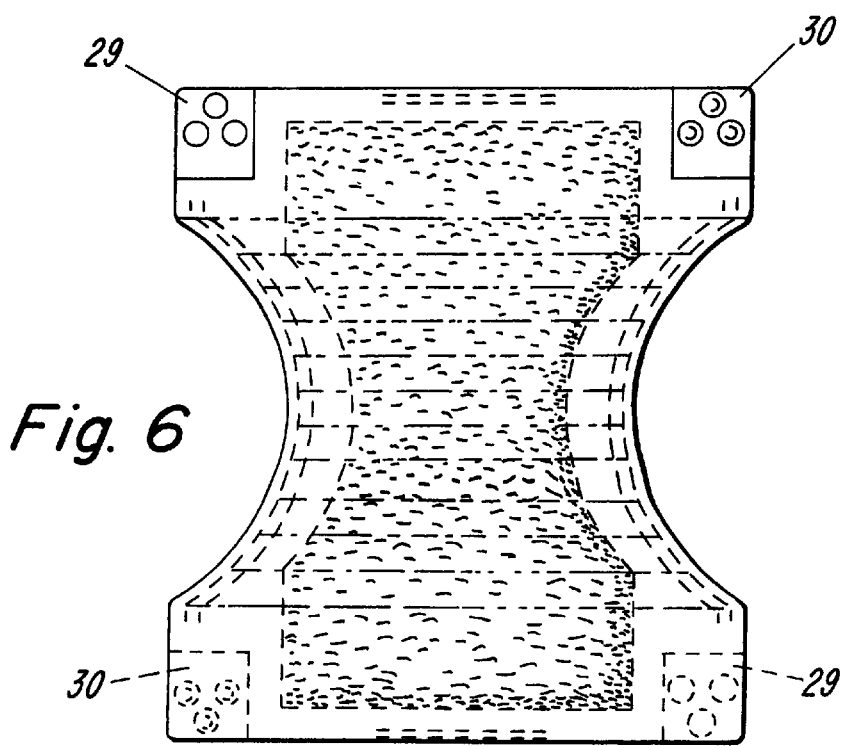
FIG. 6 illustrates schematically a preferred position of the discrete locking-element carrying pieces on the finished article.
Figure 7A:
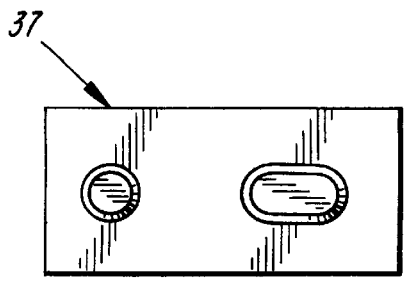
FIG. 7(a) shows a plan view of the locking element of FIG. 2(d) mounted on a discrete piece of material.
Figure 7C:
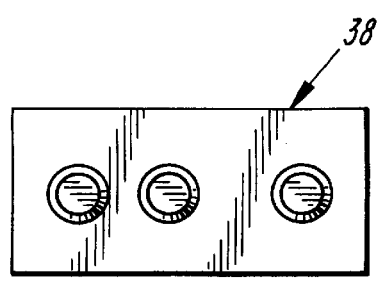
FIG. 7(c) shows a plan view of the locking element of FIG. 2(a) mounted on a discrete piece of material.
Figure 7B:
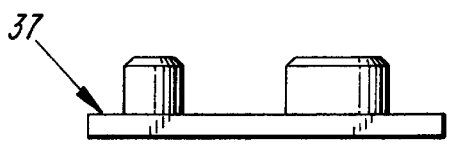
FIG. 7(b) shows a side view of the locking element of FIG. 7(a).
Figure 7D:
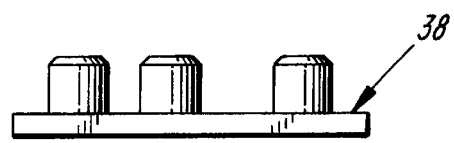
FIG. 7(d) shows a side view of the locking element of FIG. 7(c).
Figure 7E:
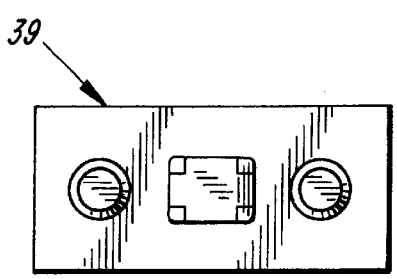
FIG. 7(e) shows a plan view of the locking element of FIG. 2(b) mounted on a discrete piece of material.
Figure 7G:
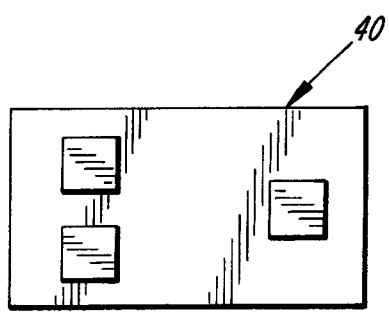
FIG. 7(g) shows a plan view of the locking element of FIG. 2(e) mounted on a discrete piece of material.
Figure 7F:
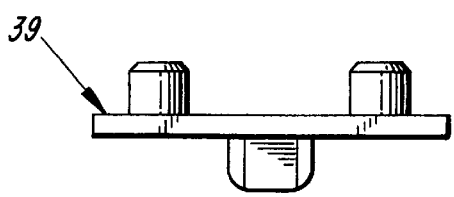
FIG. 7(f) shows a side view of the locking element of FIG. 7(e).
Figure 7H:
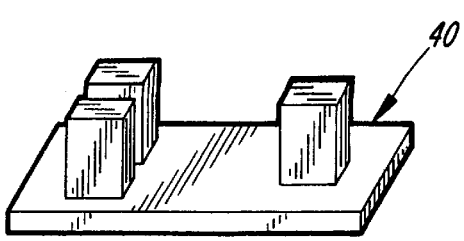
FIG. 7(h) shows a perspective view of the locking element of FIG. 7(g) of material.

FIG. 6 illustrates preferred positioning of female locking elements 29 and male locking elements 30 on an absorbent article. The configuration of the locking elements on the discrete material pieces is such that each discrete piece of material can be locked onto at least the two adjacent discrete material pieces on the absorbent article. This locking element configuration enables a used article which has been rolled up to enclose its urine and faeces content to be fastened and sealed in a desired fashion. The locking elements on one and the same respective end part are disposed on opposite side surfaces of the article to the locking elements at the opposite respective end part.

FIGS. 7(a)–(h) illustrates different element configurations for the fastener means 37–40, and different distributions between male and female elements on the discrete material pieces. In FIGS. 7(a)–(h), each fastener means is shown in two views, each rotated through 90° in relation to the other. For instance, the fastener means 37 of FIG. 2(d) and FIGS. 7(a) and (b) includes a circular element and an elliptical element. The means 38 of FIG. 2(*a*) and FIGS. 7(*c*) and (*d*) includes three circular locking elements in a configuration in which two elements form a close pair spaced from the third element. The fastener means 39 of FIG. 2(*b*) and FIGS. 7(*e*) and (*f*) includes three locking elements, where one element is turned through 180° in relation to the other two elements. The fastener means 40 of FIG. 2(*e*) and FIGS. 7(*g*) and (*h*) is a variant of the element configuration of the fastener means 38.

Different combinations of the aforesaid embodiments are conceivable. For instance, as before mentioned, the locking ability of all embodiments can be improved by applying nonwoven material or some other friction enhancing material on the male locking elements or in the female locking elements.

The invention can also be applied on pants which are intended to support absorbent diaper inserts.

It will be understood that the invention is not restricted to the aforedescribed and illustrated exemplifying embodiments thereof and that the invention can be applied to other embodiments within the scope of the inventive concept.

What is claimed is:

1. An absorbent article comprising a fastener device closing the absorbent article, wherein the fastener device includes mutually coacting parts in the form of female elements and male elements which fit into the female elements and which when closing or fastening the fastener device are pressed into the female elements and held firmly therein by friction and by means of a so-called snap-function, i.e. a function achieved by virtue of the mutual configuration of said elements, wherein the female element has an internal configuration which is so narrow at at least one location as to result in temporary elastic deformation when the male element is pressed into said female element, whereafter the elements return to there respective original shapes, the fastener device being comprised of discrete pieces of material, e.g. discrete strips, which are placed in mutually corresponding pairs on the absorbent article, whereby the female and the male elements are formed in said material pieces; said elements being configured so that each male element can be inserted into a corresponding female element and held firmly therein by virtue of a snap action, i.e. by virtue of the mutual configurations of said elements, the female element having a cross-sectional size which at at least one location is so small as to result temporarily in elastic deformation as the male element is pressed thereinto, whereafter the elements return to their respective original shapes; wherein each discrete piece of material provided with said retaining elements has a form such that said material piece can only be attached to a respective receiving discrete material piece in one specific orientation; and in that at least the male and female locking elements are covered with nonwoven material.

2. The absorbent article according to claim 1, wherein the locking elements have a configuration, size variation between the pairs of corresponding locking elements, distribution of female and male elements on each strip or corresponding piece of material, or a combination of these features so that the mutually corresponding pairs of discrete pieces of material on the absorbent article can only be attached to one another in one specific orientation.

3. The absorbent article according to claim 1, wherein the discrete pieces of materials have zones of lower flexural resistance around the locking elements than in other parts of said pieces.

4. The absorbent article according to claim 1, wherein at least the female locking elements are closed at an end which is positioned away from the vertical plane to the discrete piece of material in which said elements have been formed.

5. The absorbent article according to claim 1, wherein the discrete pieces of material are applied in pairs on the back surface of the ultimate absorbent article and on the front surface of said absorbent article, such that when said elements are locked, there will be formed an overlap such that in the waist part of the finished absorbent article the two discrete material pieces placed on the rear part of the article will preferably overlap the two discrete material pieces placed on the front part of said article.

6. The absorbent article of claim 1, wherein the absorbent article is in the form of a diaper.

7. The absorbent article of claim 1, wherein the absorbent article is in the form of a sanitary napkin.

8. The absorbent article of claim 1, wherein the discrete pieces of material are made of thermoplastic material.

9. The absorbent article of claim 1, wherein the whole of the discrete pieces of material in which said locking elements are formed are covered with nonwoven material.

\* \* \* \* \*